United States Patent
Johnston

(10) Patent No.: US 9,522,041 B2
(45) Date of Patent: Dec. 20, 2016

(54) CURRENT-FED PUSH-PULL CONVERTER WITH PASSIVE VOLTAGE CLAMP

(71) Applicant: COVIDIEN LP, Mansfield, MA (US)

(72) Inventor: Mark A. Johnston, Boulder, CO (US)

(73) Assignee: COVIDIEN LP, Mansfield, MA (US)

(*) Notice: Subject to any disclaimer, the term of this patent is extended or adjusted under 35 U.S.C. 154(b) by 390 days.

(21) Appl. No.: 14/144,850

(22) Filed: Dec. 31, 2013

(65) Prior Publication Data

US 2014/0114303 A1 Apr. 24, 2014

Related U.S. Application Data

(63) Continuation of application No. 12/823,703, filed on Jun. 25, 2010, now Pat. No. 8,617,154.

(51) Int. Cl.
*A61B 18/12* (2006.01)
*A61B 18/18* (2006.01)
(Continued)

(52) U.S. Cl.
CPC ........... *A61B 18/18* (2013.01); *A61B 18/1206* (2013.01); *A61B 18/1233* (2013.01); *A61B 18/1442* (2013.01); *A61B 18/16* (2013.01); *A61B 2018/0066* (2013.01); *A61B 2018/00345* (2013.01); *A61B 2018/00404* (2013.01); *A61B 2018/00577* (2013.01); *A61B 2018/00619* (2013.01); *A61B 2018/00642* (2013.01); *A61B 2018/00702* (2013.01);
(Continued)

(58) Field of Classification Search
CPC . A61B 18/12; A61B 18/1206; A61B 18/1233; A61B 2018/126; A61B 2018/1286
See application file for complete search history.

(56) References Cited

U.S. PATENT DOCUMENTS 3,601,126 A * 8/1971 Estes .......................... G05F 1/12
606/35
3,675,655 A * 7/1972 Sittner .................... A61B 18/12
606/35
(Continued)

FOREIGN PATENT DOCUMENTS

DE 3604823 A1 8/1987
DE 3904558 A1 8/1990
(Continued)

OTHER PUBLICATIONS

Vallfors et al., "Automatically Controlled Bipolar Electrosoagulation-'COA-COMP'", Neurosurgical Review 7:2-3 (1984) pp. 187-190.
(Continued)

*Primary Examiner* — Michael Peffley

(57) ABSTRACT

An electrosurgical generator configured to output radio frequency (RF) energy having a current-source type behavior is provided. The generator has a buck converter having a voltage source, at least one switch and an inductor. The generator also has an RF stage configured to output the RF energy. A sensor circuit configured to measure at least one parameter of the RF energy and a controller configured to receive the measured parameter from the sensor circuit and control the output of the electrosurgical generator based on the measured parameter may also be provided in the electrosurgical generator.

7 Claims, 3 Drawing Sheets

(51) Int. Cl.
  *A61B 18/14* (2006.01)
  *A61B 18/16* (2006.01)
  *A61B 18/00* (2006.01)
(52) U.S. Cl.
  CPC .............. *A61B 2018/00779* (2013.01); *A61B 2018/00827* (2013.01); *A61B 2018/00875* (2013.01); *A61B 2018/00892* (2013.01); *A61B 2018/00958* (2013.01)

(56) References Cited

U.S. PATENT DOCUMENTS

| | | | |
|---|---|---|---|
| 5,633,578 | A | 5/1997 | Eggers et al. |
| 5,658,322 | A | 8/1997 | Fleming |
| 5,843,099 | A | 12/1998 | Nichols et al. |
| 6,222,356 | B1 | 4/2001 | Taghizadeh-Kaschani |
| 6,723,091 | B2 | 4/2004 | Goble et al. |
| 7,083,636 | B2 | 8/2006 | Kortenbach |
| 7,244,255 | B2 | 7/2007 | Daners et al. |
| 7,269,034 | B2 * | 9/2007 | Schlecht ............... H02M 3/335 363/21.06 |
| 7,270,664 | B2 | 9/2007 | Johnson et al. |
| 7,300,436 | B2 | 11/2007 | Penny et al. |
| D574,323 | S | 8/2008 | Waaler |
| 7,564,702 | B2 | 7/2009 | Schlecht |
| 8,603,107 | B2 | 12/2013 | Fischvogt |
| 2003/0083695 | A1 | 5/2003 | Morris et al. |
| 2005/0113820 | A1 * | 5/2005 | Goble ................ A61B 18/1206 606/34 |
| 2005/0177176 | A1 | 8/2005 | Gerbi et al. |
| 2008/0013350 | A1 * | 1/2008 | Goliszek ............ A61B 18/1206 363/68 |
| 2010/0137854 | A1 * | 6/2010 | Hosier ................... A61B 18/12 606/33 |
| 2011/0170321 | A1 | 7/2011 | Schall et al. |
| 2011/0213354 | A1 | 9/2011 | Smith |
| 2012/0053578 | A1 * | 3/2012 | Schall ................ A61B 18/1206 606/33 |

FOREIGN PATENT DOCUMENTS

| | | |
|---|---|---|
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 10 2008058737 A1 | 4/2010 |
| EP | 0 246 350 A1 | 11/1987 |
| EP | 267403 A2 | 5/1988 |
| EP | 296777 A2 | 12/1988 |
| EP | 310431 A2 | 4/1989 |
| EP | 325456 A2 | 7/1989 |
| EP | 336742 A2 | 10/1989 |
| EP | 390937 A1 | 10/1990 |
| EP | 0 556 705 A1 | 8/1993 |
| EP | 608609 A2 | 8/1994 |
| EP | 0 836 868 A2 | 4/1998 |
| EP | 880220 A2 | 11/1998 |
| EP | 0 882 955 A1 | 12/1998 |
| EP | 1051948 A2 | 11/2000 |
| EP | 1366724 A1 | 12/2003 |
| EP | 1498075 A1 | 1/2005 |
| EP | 1776929 A1 | 4/2007 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| SU | 166452 | 11/1964 |
| SU | 727201 A2 | 4/1980 |
| WO | 02/11634 A1 | 2/2002 |
| WO | 02/45589 A2 | 6/2002 |
| WO | 03/090635 A1 | 11/2003 |
| WO | 2006/050888 A1 | 5/2006 |

OTHER PUBLICATIONS

Sugita et al., "Bipolar Coagulator with Automatic Thermocontrol", J. Neurosurg., vol. 41, Dec. 1944, pp. 777-779.

Muller et al. "Extended Left Hemicolectomy Using the LigaSure Vessel Sealing System", Innovations That Work; Company Newsletter; Sep. 1999.

Ogden Goertzel Alternative to the Fourier Transform: Jun. 1993 pp. 485-487, Electronics World; Reed Business Publishing, Sutton, Surrey, BG vol. 99, No. 9. 1687.

Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.

Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.

Richard Wolf Medical Instruments Corp. Brochure, "Kleppinger Bipolar Forceps & Bipolar Generator", 3 pp. Jan. 1989.

Astrahan, "A Localized Current Field Hyperthermia System for Use with 192-Iridium Interstitial Implants" Medical Physics, 9 (3), May/Jun. 1982.

Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.

Geddes et al., "The Measurement of Physiologic Events by Electrical Impedence", Am. J. MI, Jan. Mar. 1964, pp. 16-27.

Cosman et al., "Methods of Making Nervous System Lesions", In William RH, Rengachary SS (eds): Neurosurgery, New York: McGraw-Hill, vol. 111, (1984), pp. 2490-2499.

Anderson et al., "A Numerical Study of Rapid Heating for High Temperature Radio Frequency Hyperthermia" International Journal of Bio-Medical Computing, 35 (1994) pp. 297-307.

Benaron et al., "Optical Time-Of-Flight and Absorbance Imaging of Biologic Media", Science, American Association for the Advancement of Science, Washington, DC, vol. 259, Mar. 5, 1993, pp. 1463-1466.

Cosman et al., "Radiofrequency Lesion Generation and Its Effect on Tissue Impedance", Applied Neurophysiology 51: (1988) pp. 230-242.

Ni W. et al. "A Signal Processing Method for the Coriolis Mass Flowmeter Based on a Normalized . . . ", Journal of Applied Sciences-Yingyong Kexue Xuebao, Shangha CN, vol. 23 No. 2;(Mar. 2005); pp. 160-164.

Chicharo et al. "A Sliding Goertzel Algorith" Aug. 1996, pp. 283-297, Signal Processing, Elsevier Science Publishers B.V. Amsterdam, NL vol. 52 No. 3.

Bergdahl et al., "Studies on Coagulation and the Development of an Automatic Computerized Bipolar Coagulator" Journal of Neurosurgery 75:1, (Jul. 1991) pp. 148-151.

Cosman et al., "Theoretical Aspects of Radiofrequency Lesions in the Dorsal Root Entry Zone", Neurosurgery 15: (1984) pp. 945-950.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Medtrex Brochure—Total Control at Full Speed, "The O.R. Pro 300", 1 p. Sep. 1998.

Valleylab Brochure "Valleylab Electroshield Monitoring System", 2 pp. Nov. 1995.

Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427. cited by applicant.

Benaron et al., "Optical Time-Of-Flight and Absorbance Imaging of Biologic Media", Science, American Association for the Advance-

(56) References Cited

OTHER PUBLICATIONS ment of Science, Washington, DC, vol. 259, Mar. 5, 1993, pp. 1463-1466. cited by applicant.

* cited by examiner

CURRENT-FED PUSH-PULL CONVERTER WITH PASSIVE VOLTAGE CLAMP

CROSS REFERENCE TO RELATED APPLICATIONS

This application is a Continuation application of U.S. patent application Ser. No. 12/823,703 filed on Jun. 25, 2010 and issued as U.S. Pat. No. 8,617,154, which is expressly incorporated herein by reference in its entirety.

BACKGROUND

1. Technical Field

The present disclosure is directed to electrosurgical systems, and, in particular, to an electrosurgical system having a radio frequency (RF) output with a current-source type behavior.

2. Description of the Related Art

An electrosurgical generator is used in surgical procedures to deliver electrical energy to the tissue of a patient. When an electrode is connected to the generator, the electrode can be used for cutting, coagulating or sealing the tissue of a patient with high frequency electrical energy. During normal operation, alternating electrical current from the generator flows between an active electrode and a return electrode by passing through the tissue and bodily fluids of a patient.

The electrical energy usually has a waveform shaped to enhance its ability to cut, coagulate or seal tissue. Different waveforms correspond to different modes of operation of the generator, and each mode gives the surgeon various operating advantages. Modes may include cut, coagulate, a blend thereof, desiccate, or spray. A surgeon can easily select and change the different modes of operation as the surgical procedure progresses.

In each mode of operation, the electrosurgical power delivered to the patient is regulated to achieve the desired surgical effect. Applying more electrosurgical power than necessary results in tissue destruction and prolongs healing. Applying less than the desired amount of electrosurgical power inhibits the surgical procedure. Thus, it is desirable to control the output energy from the electrosurgical generator for the type of tissue being treated.

Different types of tissues will be encountered as the surgical procedure progresses and each unique tissue requires more or less power as a function of frequently changing tissue impedance. As different types of tissue and bodily fluids are encountered, the impedance changes and the response time of the electrosurgical control of output power must be rapid enough to seamlessly permit the surgeon to treat the tissue. Moreover, the same tissue type can be desiccated during electrosurgical treatment and thus the tissue impedance will change dramatically in the space of a very brief time. The electrosurgical output power control needs to respond to a rapid change in impedance to effectively treat tissue.

Electrosurgical generators generally have a voltage-source type output behavior. In the voltage-source type output behavior, the delivered output current is inversely proportional to the load (e.g., tissue) impedance Electrosurgical generator may also have an RF output with a current-source type behavior where the delivered current is independent of the load impedance. An example of an electrosurgical generator with a current-source type behavior may be a current-fed push-pull converter. A current-source type generator has a disadvantage in that, as the impedance of the tissue increases, the open-circuit voltage may reach unacceptably high levels.

SUMMARY

The present disclosure provides for an electrosurgical generator configured to output radio frequency (RF) energy having a current-source type behavior. The generator includes a buck converter having a voltage source, at least one switch and an inductor. The generator also includes an RF stage configured to output the RF energy, a sensor circuit configured to measure one or more parameters of the RF energy, and a controller configured to receive the measured parameter from the sensor circuit and control the output of the electrosurgical generator based on the measured parameter.

The RF stage includes a transformer having one or more primary windings and a secondary winding. The electrosurgical generator may also include an active element coupled between the voltage source and a center tap of the primary winding. The active element may be a diode, a Zener diode or a field effect transistor.

In another embodiment, an electrosurgical generator configured to output radio frequency (RF) energy having a current-source type behavior is provided that includes a buck converter having a voltage source, one or more switches and an inductor, an RF stage configured to output the RF energy, and an active element coupled between the voltage source and the RF stage.

The RF stage includes a transformer having one or more primary windings and a secondary winding. The active element may be coupled between the voltage source and a center tap of the primary winding. The active element may be a diode, a Zener diode or a field effect transistor. The electrosurgical generator may also include a sensor circuit configured to measure one or more parameters of the RF energy and a controller configured to receive the measured parameter from the sensor circuit and control the output of the electrosurgical generator based on the measured parameter.

In yet another embodiment, an electrosurgical generator configured to output radio frequency (RF) energy having a current-source type behavior is provided that includes a buck converter having a voltage source, one or more switches and an inductor. The electrosurgical generator also includes a transformer having at least one primary winding, a secondary winding and at least one tertiary winding.

The electrosurgical generator may also have a sensor circuit configured to measure one or more parameters of the RF energy, and a controller configured to receive the measured parameter from the sensor circuit and control the output of the electrosurgical generator based on the measured parameter.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1A:
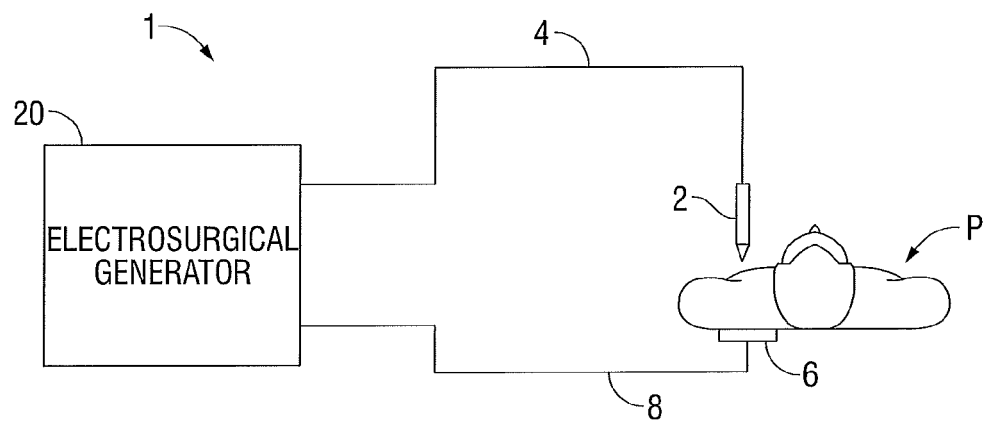
FIGS. 1A-1B are schematic block diagrams of an electrosurgical system according to an embodiment of the present disclosure for use with various instrument types.

Particular embodiments of the present disclosure are described hereinbelow with reference to the accompanying drawings; however, it is to be understood that the disclosed embodiments are merely exemplary of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

The generator according to the present disclosure can perform ablation, monopolar and bipolar electrosurgical procedures, including vessel sealing procedures. The generator may include a plurality of outputs for interfacing with various electrosurgical instruments (e.g., a monopolar active electrode, return electrode, bipolar electrosurgical forceps, footswitch, etc.). Further, the generator includes electronic circuitry configured for generating radio frequency power specifically suited for various electrosurgical modes (e.g., cutting, blending, division, etc.) and procedures (e.g., monopolar, bipolar, vessel sealing).

FIG. 1A is a schematic illustration of a monopolar electrosurgical system 1 according to one embodiment of the present disclosure. The system 1 includes an electrosurgical instrument 2 having one or more electrodes for treating tissue of a patient P. The instrument 2 is a monopolar type instrument including one or more active electrodes (e.g., electrosurgical cutting probe, ablation electrode(s), etc.). Electrosurgical RF energy is supplied to the instrument 2 by a generator 20 via a supply line 4, which is connected to an active terminal (not shown) of the generator 20, allowing the instrument 2 to coagulate, ablate and/or otherwise treat tissue. The energy is returned to the generator 20 through a return electrode 6 via a return line 8 at a return terminal (not shown) of the generator 20. The active terminal and the return terminal are connectors configured to interface with plugs (not explicitly shown) of the instrument 2 and the return electrode 6, which are disposed at the ends of the supply line 4 and the return line 8, respectively.

The system 1 may include a plurality of return electrodes 6 that are arranged to minimize the chances of tissue damage by maximizing the overall contact area with the patient P. In addition, the generator 20 and the return electrode 6 may be configured for monitoring so-called "tissue-to-patient" contact to insure that sufficient contact exists therebetween to further minimize chances of tissue damage. In one embodiment, the active electrode 6 may be used to operate in a liquid environment, wherein the tissue is submerged in an electrolyte solution.

The generator 20 includes suitable input controls (e.g., buttons, activators, switches, touch screen, etc.) for controlling the generator 20. In addition, the generator 20 may include one or more display screens for providing the user with variety of output information (e.g., intensity settings, treatment complete indicators, etc.). The controls allow the user to adjust power of the RF energy, waveform, as well as the level of maximum arc energy allowed that varies depending on desired tissue effects and other parameters to achieve the desired waveform suitable for a particular task (e.g., coagulating, tissue sealing, intensity setting, etc.). The instrument 2 may also include a plurality of input controls that may be redundant with certain input controls of the generator 20. Placing the input controls at the instrument 2 allows for easier and faster modification of RF energy parameters during the surgical procedure without requiring interaction with the generator 20.

Figure 1B:
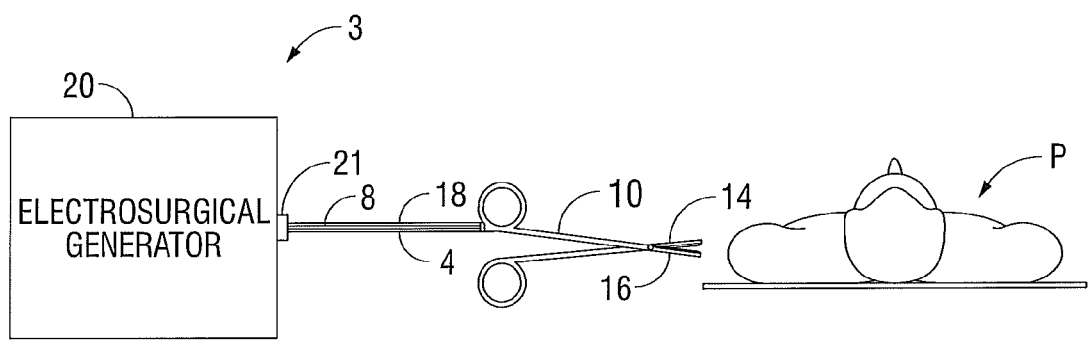

FIG. 1B is a schematic illustration of a bipolar electrosurgical system 3 according to the present disclosure. The system 3 includes a bipolar electrosurgical forceps 10 having one or more electrodes for treating tissue of a patient P. The electrosurgical forceps 10 include opposing jaw members having an active electrode 14 and a return electrode 16, respectively, disposed therein. The active electrode 14 and the return electrode 16 are connected to the generator 20 through cable 18, which includes the supply and return lines 4 and 8 coupled to the active and return terminals, respectively. The electrosurgical forceps 10 are coupled to the generator 20 at a connector 21 having connections to the active and return terminals (e.g., pins) via a plug disposed at the end of the cable 18, wherein the plug includes contacts from the supply and return lines 4, 8.

Figure 2:
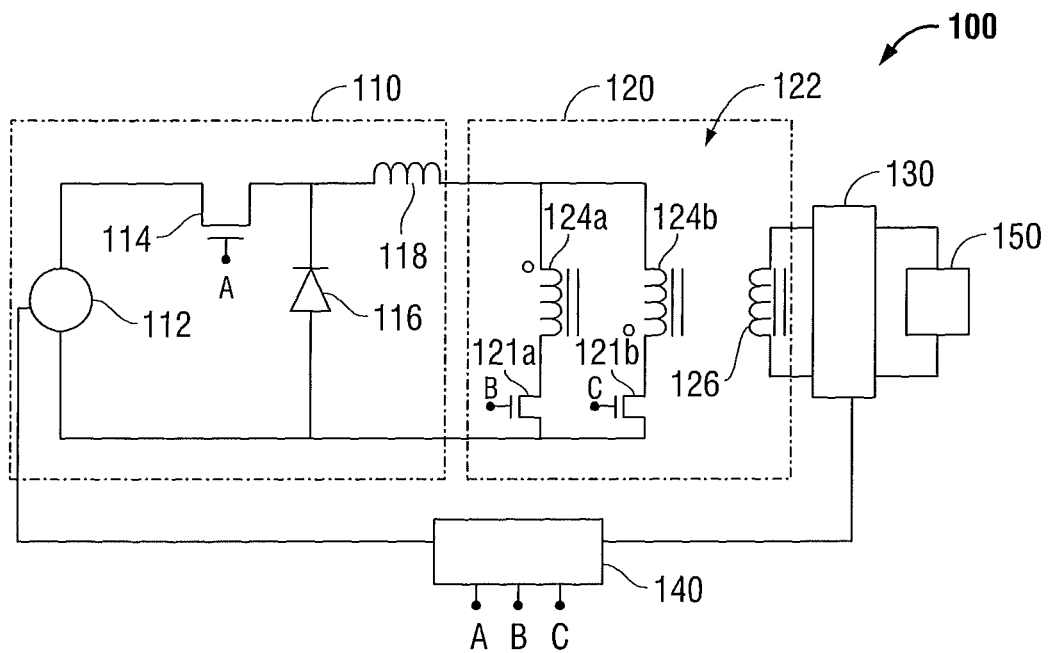
FIG. 2 is a schematic diagram of a current-fed push-pull converter.

FIG. 2 is a schematic illustration of a generator 100 that may output RF energy having a current-source type behavior according to an embodiment of the present disclosure. As shown in FIG. 2, generator 100 has a buck converter 110 and an RF stage 120. Buck converter 110 is a switched mode power supply that may use two switches (e.g., a transistor and a diode). Buck converter 110 has a voltage source 112 that may be a power supply or battery, a field effect transistor (FET) 114, diode 116 and an inductor 118. The buck converter alternates between connecting inductor 118 to voltage source 112 using FET 114 and diode 116 to store energy in inductor 118 and discharge energy from inductor 118 into the load.

RF stage 120 includes a transformer 122 having primary windings 124a and 124b and secondary winding 126. Primary windings 124a and 124b are coupled to FETs 121a and 121b, respectively. Secondary winding 126 of transformer 122 outputs RF energy to a load 150 (e.g., tissue). The turns ratio for transformer 122 may be varied to limit the maximum voltage output of secondary winding 126. The controller 140 includes a microprocessor operably connected to a memory, which may be volatile type memory (e.g., RAM) and/or non-volatile type memory (e.g., flash media, disk media, etc.). The controller 140 includes an output port that is operably connected to FETs 114, 121a and 121b allowing the controller 140 to control the output of the generator 100 according to either open and/or closed control loop schemes. Those skilled in the art will appreciate that the microprocessor may be substituted by any logic processor or analog circuitry (e.g., control circuit) adapted to perform the calculations discussed herein.

The generator 100 may implement a closed and/or open loop control schemes that include a sensor circuit 130 having a plurality of sensors measuring a variety of tissue and energy properties (e.g., tissue impedance, tissue temperature, output current and/or voltage, etc.), and providing feedback to the controller 140. A current sensor can be disposed at either the active or return current path or both and voltage can be sensed at the active electrode(s). The controller 140 then transmits appropriate signals to control the output of generator 100. The controller 140 also receives input signals from the input controls of the generator or the instrument. The controller 140 utilizes the input signals to adjust power output by the generator 100 and/or performs other control functions thereon.

The sensor circuit 130 measures the electrical current (I) and voltage (V) supplied by transformer 122 in real time to characterize the electrosurgical process during both the matching sinusoidal and non-sinusoidal durations for a predetermined sampling period, the former being of short duration (e.g., half a cycle) and the latter being of long duration (e.g., about 15 cycles). This allows for the measured electrical properties to be used as dynamic input control variables to achieve feedback control. The current and voltage values may also be used to derive other electrical parameters, such as power (P=V*I) and impedance (Z=V/I). The sensor circuit 130 also measures properties of the current and voltage waveforms and determines the shape thereof.

Using a generator with a current-source type behavior as described above with regard to FIG. 2 has many advantages over generators employing voltage-source type behavior. For instance, generators having a voltage-source type behavior apply a constant voltage to tissue during an electrosurgical procedure. As voltage is applied to tissue, the tissue impedance changes thereby changing the tissue current density. Because tissues in a given cross section have different impedances, there will be different current densities in the different tissues resulting in different heating patterns in the tissue. Thus may lead to non-uniform heating and tissue trauma. By providing a constant current using a generator with a current-source type behavior, the heating pattern for tissue can be kept constant thereby reducing the risk of non-uniform heating and tissue trauma.

Figure 3:
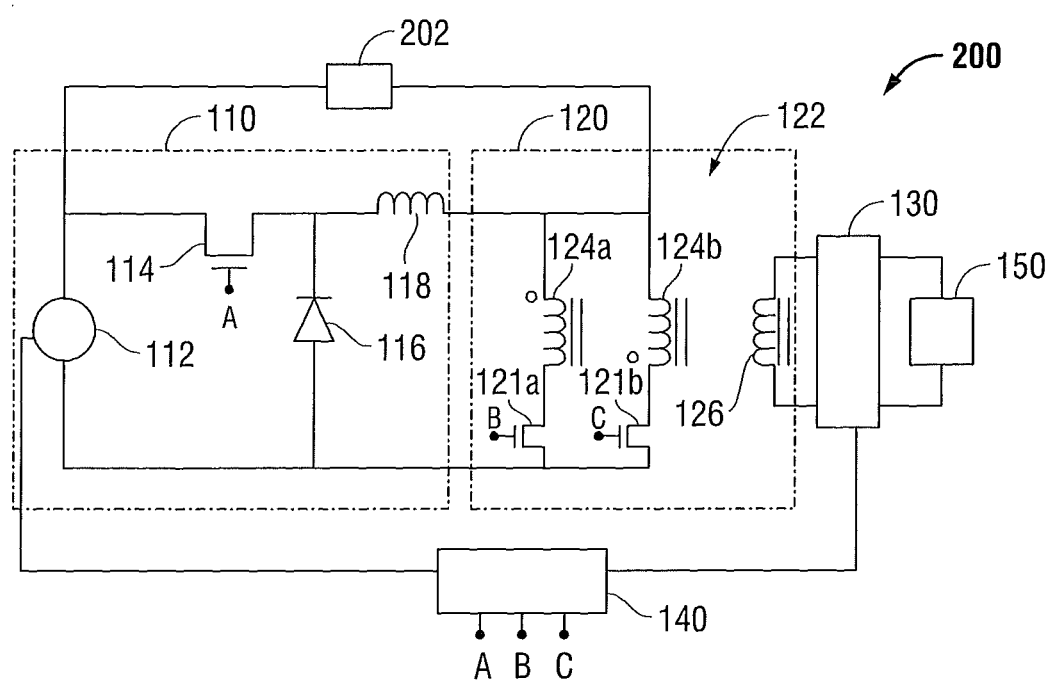
FIG. 3 is a schematic diagram of a current-fed push-pull converter according to an embodiment of the present disclosure.

FIG. 3 is a schematic illustration of a generator 200 that may output RF energy having a current-source type behavior according to another embodiment of the present disclosure. Generator 200 is similar to generator 100 of FIG. 2 and, as such, the operation of generator 200 is similar to the operation of generator 100 described above. Generator 200 further includes an active device 202 coupled between center tap 204 of transformer 122 and voltage source 112. Active device 202 limits the maximum voltage seen across the primary winding of transformer 122 thereby limiting the reflected voltage in the secondary winding of transformer 122.

Active device 202 may be a diode, a Zener diode or an FET. If active device 202 is a diode, the anode of the diode is coupled to the center tap 204 of transformer 202 and the cathode is coupled to voltage source 112 so that the diode is in a reverse-biased configuration. A reverse-biased diode prevents current from going through the diode, due to an expanded depletion region. The ability of a diode to withstand reverse-bias voltages is limited, as it is for any insulator. If the applied reverse-bias voltage becomes too great, the diode will experience a condition known as breakdown, which is usually destructive.

A Zener diode permits current in the forward direction like a normal diode, but also in the reverse direction if the voltage is larger than the breakdown voltage. Different Zener diodes may be used to achieve different voltage drops across the Zener diode thereby adjusting the maximum voltage that would be seen across the primary windings of transformer 122.

Generator 200 has similar advantages as described above with regard to FIG. 2. Additionally, generator 200 uses an active element to limit the maximum voltage seen across the primary winding. Limiting the maximum voltage seen across the primary winding also limits the maximum voltage outputted by the secondary winding. Generator 200 also has an additional advantage in that it can be customized by a user by using different active elements to achieve specific voltage drops to limit the voltage seen across the primary winding and the voltage outputted by the secondary winding.

Figure 4:
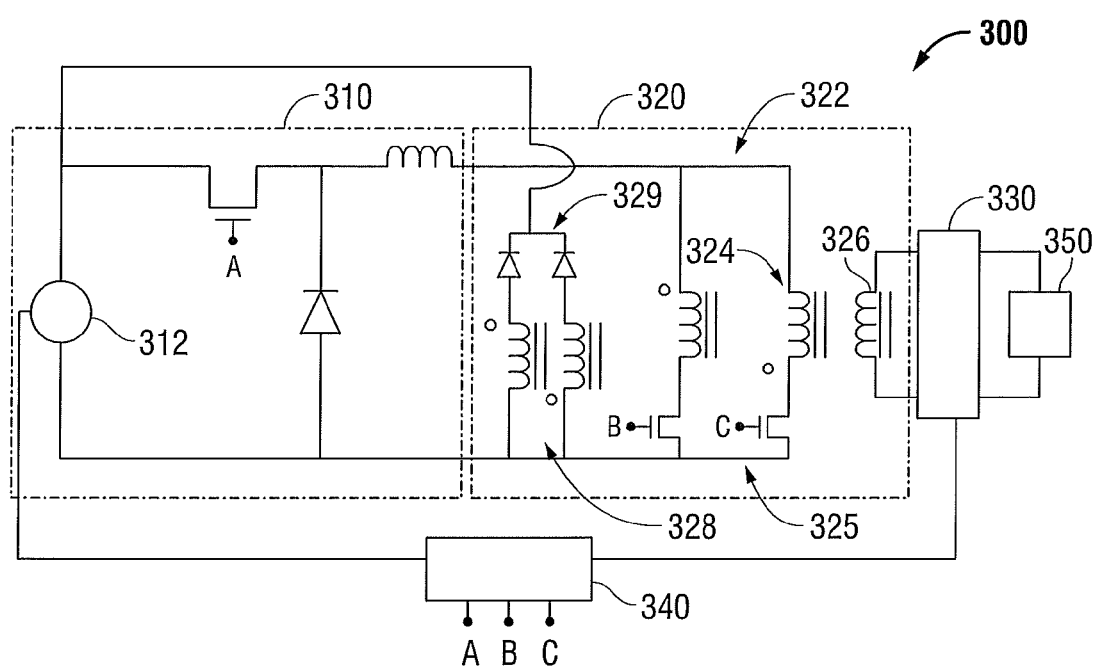
FIG. 4 is a schematic diagram of a current-fed push-pull converter according to another embodiment of the present disclosure.

FIG. 4 is a schematic illustration of a generator 300 that may output RF energy having a current-source type behavior according to another embodiment of the present disclosure. Generator 300 has a buck converter 310 and an RF stage 320. RF stage 320 includes a transformer 322 that has primary windings 324 in series with FETs 325. Secondary winding 326 outputs RF energy to load 350. Transformer 322 may include one or more tertiary windings 328 that are clamped to voltage source 312 of buck converter 310 via one or more active elements 329 such as a diode, Zener diode or FET. The turns ratio for transformer 322 may be varied to limit the maximum output voltage of transformer 322 from secondary winding 326.

As described above, a sensor circuit 330 may be provided that measures the electrical current (I) and voltage (V) supplied by transformer 322 in real time. This allows for the measured electrical properties to be used as dynamic input control variables to achieve feedback control. The current and voltage values may also be used to derive other electrical parameters, such as power (P=V*I) and impedance (Z=V/I). The sensor circuit also measures properties of the current and voltage waveforms and determines the shape thereof.

Generator 300 may also include a controller 340 similar to controller 140 described above. Controller 340 controls the operation of FETs 314 and 325 to control the RF energy output of generator 300. Controller 340 may also receive a signal from sensor circuit 330 and adjust the output of generator 300 based on the received signal.

Generator 300 utilizes a tertiary winding on transformer 322 instead of an active element, as described above with regard to FIG. 3, to limit the maximum voltage output of the secondary winding. Active elements tend to lose power through heat thereby resulting in lower power efficiency. Providing a tertiary winding on the transformer would also limit the voltage outputted by the secondary winding while maintaining higher power efficiency.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. The claims can encompass embodiments in hardware, software, or a combination thereof. Those skilled in the art will envision other modifications within the scope and spirit of the claims appended hereto.

What is claimed is:

1. An electrosurgical generator configured to output radio frequency (RF) energy, the generator comprising:
    a switched mode power supply having a voltage source, at least one switch, and an inductor; and
    a transformer having at least one primary winding, a secondary winding, and at least one tertiary winding, the tertiary winding clamped directly to the voltage source of the switched mode power supply.

2. The electrosurgical generator of claim 1, further comprising an active element coupled between the voltage source and the tertiary winding.

3. The electrosurgical generator of claim 2, wherein the active element is a field effect transistor.

4. The electrosurgical generator of claim 2, wherein the active element is a diode.

5. The electrosurgical generator of claim 2, wherein the active element is a Zener diode.

6. The electrosurgical generator of claim 2, further comprising:
   a sensor circuit configured to measure at least one parameter of the RF energy; and
   a controller configured to receive the measured parameter from the sensor circuit and control the output of the electrosurgical generator based on the measured parameter.

7. The electrosurgical generator of claim 1, wherein the voltage source is a battery.

* * * * *